United States Patent
Hewawasam et al.

(10) Patent No.: US 6,469,042 B1
(45) Date of Patent: Oct. 22, 2002

(54) FLUORO OXINDOLE DERIVATIVES AS MODULATORS IF KCNQ POTASSIUM CHANNELS

(75) Inventors: Piyasena Hewawasam, Middletown, CT (US); Pierre Dextraze, Laprairie (CA); Valentin K. Gribkoff, Wallingford, CT (US); Gene G. Kinney, Collegeville, CT (US); Steven I. Dworetzky, Middlefield, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/075,522

(22) Filed: Feb. 14, 2002

Related U.S. Application Data
(60) Provisional application No. 60/270,112, filed on Feb. 20, 2001.

(51) Int. Cl.[7] .................. A61K 3/405; C07D 209/12; C07D 209/90
(52) U.S. Cl. .................. 514/411; 514/418; 548/450; 548/469
(58) Field of Search ............... 548/450, 469; 514/418, 411

(56) References Cited

U.S. PATENT DOCUMENTS
| | | | | |
|---|---|---|---|---|
| 5,565,483 A | * | 10/1996 | Hewawasam | 514/411 |
| 5,602,169 A | * | 2/1997 | Hewawasam | 514/418 |
| 5,892,106 A | * | 4/1999 | Hewawasam | 562/435 |

* cited by examiner

Primary Examiner—Deborah C. Lambkin
Assistant Examiner—Rei-Tsang Shiau
(74) Attorney, Agent, or Firm—Aldo A. Algieri

(57) ABSTRACT

There is provided novel 3-fluoro-3-phenyl oxindole derivatives of Formula I

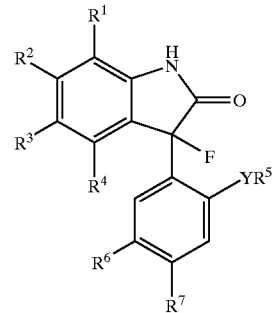

wherein
$R^1$, $R^2$, $R^3$ and $R^4$ each are independently hydrogen, $C_{1-4}$ alkyl, halogen, fluoromethyl, trifluoromethyl, phenyl, 4-methylphenyl or 4-trifluoromethylphenyl;

$R^5$ is $C_{1-6}$ alkyl optionally substituted with one to three same or different groups selected from fluoro and chloro, provided $R^5$ is not $C_{1-6}$ alkyl when Y is O;

Y is O or S; and $R^6$ and $R^7$ each are independently hydrogen, chloro, bromo or trifluoromethy;

which are openers of the KCNQ potassium channels and are useful in the treatment of disorders which are responsive to the opening of the KCNQ potassium channels.

12 Claims, No Drawings

FLUORO OXINDOLE DERIVATIVES AS MODULATORS IF KCNQ POTASSIUM CHANNELS

CROSS-REFERENCE TO RELATED APPLICATIONS

This is a non-provisional application which claims the benefit of U.S. Provisional Application No. 60/270,112 filed Feb. 20, 2001.

FIELD OF THE INVENTION

The present invention is directed to novel 3-fluoro-3-phenyl oxindole derivatives which are modulators of KCNQ potassium channels and are therefore useful in treating disorders responsive to the modulation of the potassium channels. The present invention also provides a method of treatment with the novel 3-fluoro oxindole derivatives and to pharmaceutical compositions thereof.

BACKGROUND OF THE INVENTION

Potassium ($K^+$) channels are considered to be the most diverse class of ion channels and have several critical roles in cell function. This has been demonstrated in neurons where $K^+$ channels are responsible, in part, for determining cell excitability by contributing to membrane repolarization following depolarization, resting membrane potential, and regulation of neurotransmitter release. The M-current has long been described, by electrophysiology recording methods and by pharmacology, as a dominant conductance in controlling neuronal excitability. Pharmacological activation or suppression of M-currents by small molecules could have profound effects in controlling neuronal excitability. Recently, Wang et al. (1998, *Science*, 282:1890–1893) reported that co-assembly of the KCNQ2 and KCNQ3 potassium channels underlies the native M-current in neurons.

Activation or opening of the KCNQ channel(s), particularly the KCNQ2 or KCNQ2/3 channel(s), mutated or wild type, may prove to be beneficial in increasing hyperpolarization of neurons, thereby resulting in protection from abnormal synchronous firing during a migraine attack. The present invention provides a solution to the problem of abnormal synchronous firing of neurons related to migraine headache by demonstrating that modulators, preferably openers, of KCNQ potassium channels increases hyperpolarization of neurons which protects against abnormal synchronous neuron firing involved in migraine attacks.

Although the symptom pattern varies among migraine sufferers, the severity of migraine pain justifies a need for vigorous, yet safe and effective, treatments and therapies for the great majority of cases. Needed in the art are agents that can be used to combat and relieve migraine (and diseases similar to and mechanistically related to migraine), and even prevent the recurrence of migraine. Also needed are anti-migraine agents which are effective in the treatment of acute migraine, as well as in the prodrome phase of a migraine attack. Thus, a clear goal in the art is to discover new, safe, nontoxic and effective anti-migraine compounds for use as drugs, and in anti-migraine compositions and treatments.

Because migraine afflicts a large percentage of the population, there is a need to discover compounds and agents that are useful in therapeutics and treatments, and as components of pharmaceutical compositions, for reducing, ameliorating, or alleviating the pain and discomfort of migraine headache and other symptoms of migraine. The present invention satisfies such a need by providing compounds that function as openers of the KCNQ family of potassium channel proteins to serve as anti-migraine agents or drugs and to comprise compositions to treat migraine, as described herein.

A number of substituted oxindoles have been disclosed as neuroanabolic agents by H. Kuch et al. in U.S. Pat. No. 4,542,148, issued Sep. 17, 1985 and U.S. Pat. No. 4,614,739, issued Sep. 30, 1986.

3-Substituted oxindole derivatives with utility as openers of the large conductance calcium-activated potassium channels have been disclosed by Hewawasam, P; Meanwell, N. A.; and Gribkoff, V. K. in U.S. Pat. No. 5,565,483, issued Oct. 15, 1996 and U.S. Pat. No. 5,602,169, issued Feb. 11, 1997, both of which are disclosed to be useful in the treatment of disorders that are responsive to the opening of the large conductance calcium-activated potassium channels, also called maxi-K channels. Because of their voltage and calcium dependence, maxi-K channels are distinct from KCNQ potassium channels, which are only voltage dependent. In addition, the pharmacology and kinetics of maxi-K channels versus KCNQ channels are frequently quite different, and the large conductance or maxi-K channels are responsive to the opener compounds specifically disclosed in U.S. Pat. No. 5,565,483. Thus, the compounds and their uses described in these patents are distinct from those of the present invention.

SUMMARY OF THE INVENTION

The present invention provides novel 3-fluoro oxindole derivatives having the general Formula I

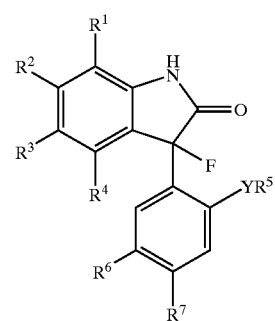

wherein $R^1$, $R^2$, $R^3$, $R^4$, $R^5$, $R^6$, $R^7$ and Y are as defined below, or a nontoxic pharmaceutically acceptable salt, solvate or hydrate thereof which are openers or activators of KCNQ potassium channels. The present invention also provides pharmaceutical compositions comprising said 3-fluoro oxindole derivatives and to the method of treatment of disorders sensitive to KCNQ potassium channel opening activity such as migraine.

DETAILED DESCRIPTION OF THE INVENTION

The present invention provides novel 3-fluoro oxindole derivatives which are modulators of the KCNQ potassium channels and which have the general Formula I

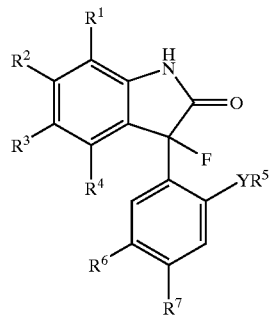

wherein

R[1], R[2], R[3] and R[4] each are independently hydrogen, $C_{1-4}$ alkyl, halogen, fluoromethyl, trifluoromethyl, phenyl, 4-methylphenyl or 4-trifluoromethylphenyl;

R[5] is $C_{1-6}$ alkyl optionally substituted with one to three same or different groups selected from fluoro and chloro, provided R[5] is not $C_{1-6}$ alkyl when Y is O;

Y is O or S; and

R[6] and R[7] each are independently hydrogen, chloro, bromo or trifluoromethyl.

The present invention also provides a method for the treatment or alleviation of disorders associated with KCNQ potassium channel polypeptides and, in particular, human KCNQ potassium channel polypeptides which are especially involved in reducing or alleviating migraine or a migraine attack, which comprises administering together with a conventional adjuvant, carrier or diluent a therapeutically effective amount of a compound of Formula I.

The term "$C_{1-6}$ alkyl" as used herein and in the claims means straight or branched chain alkyl groups such as methyl, ethyl, propyl, isopropyl, butyl, isobutyl, tert-butyl, pentyl, 4-methylbutyl, hexyl and the like. The term "$C_{1-4}$ alkyl" as used herein and in the claims means straight or branched chain alkyl groups such as methyl, ethyl, propyl, isopropyl, butyl, isobutyl, and tert-butyl. The term "halogen" as used herein and in the claims is intended to include bromine, chlorine, iodine and fluorine.

As the compounds of the present invention possess an asymmetric carbon atom at the 3-position of the oxindole ring, the present invention includes the racemate as well as the individual enantiomeric forms of the compounds of Formula I as described herein and in the claims. Preferred embodiments of compounds of Formula I are the racemate and the single enantiomer which includes mostly the one stereoisomer having a (+) optical rotation is most preferred. Mixtures of isomers of the compounds of the examples or chiral presursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns, according to procedures described herein.

Certain of the compounds of the present invention can exist in unsolvated forms as well as solvated forms including hydrated forms such as monohydrate, dihydrate, trihydrate, hemihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the method that is sufficient to show a meaningful patient benefit, i.e., amelioration or healing of conditions which respond to modulation of the KCNQ potassium channels. When applied to an individual active ingredient, administered alone, the term refers to that ingredient alone. When applied to a combination, the term refers to combined amounts of the active ingredients that result in the therapeutic effect, whether administered in combination, serially or simultaneously. The term "KCNQ" as used herein and in the claims means the family of KCNQ2, KCNQ3, KCNQ4, and KCNQ5 potassium channel polypeptides as well as heteromultimers of different individual family members which include but are not limited to KCNQ2/3, KCNQ2/5 and KCNQ3/5. The terms "treat, treating, treatment" as used herein and in the claims means preventing, alleviating or ameliorating diseases and/or symptoms associated with dysfunction of cellular membrane polarization and conductance of human KCNQ2, KCNQ3, KCNQ4, and KCNQ5 potassium channel polypeptides and, in particular, migraine and/or symptoms that precede a full-blown migraine attack.

Preferred compounds for use in the method of the present invention include the compounds of Formula I listed below:

(±)-3-[5-chloro-2-[(2,2,2-trifluoroethoxy)phenyl]-1,3-dihydro-3-fluoro-6-(trifluoromethyl)-2H-indol-2-one;

Isolation of (+)-3-[5-chloro-2-[(2,2,2-trifluoroethoxy)phenyl]-1,3-dihydro-3-fluoro-6-(trifluoromethyl)-2H-indol-2-one;

(±)-3-[5-chloro-2-(2,2,2-trifluoroethoxy)phenyl]-1,3-dihydro-3,6-difluoro-2H-indol-2-one;

(±)-3-[5-chloro-2-(2,2,2-trifluoroethoxy)phenyl]-1,3-dihydro-3-fluoro-6-(fluoromethyl)-2H-indol-2-one;

(±)-3-[5-chloro-2-(2,2,2-trifluoroethoxy)phenyl]-4,6-dichloro-1,3-dihydro-3-fluoro-2H-indol-2-one (±)-3-[5-chloro-2-(2,2,2-trifluoroethoxy)phenyl]-5,6-dichloro-1,3-dihydro-3-fluoro-2H-indol-2-one;

(±)-3-[5-chloro-2-(2,2,2-trifluoroethoxy)phenyl]-1,3-dihydro-3,5,6-trifluoro-2H-indol-2-one;

(±)-6-chloro-3-[5-chloro-2-(2,2,2-trifluoroethoxy)phenyl]-1,3-dihydro-3-fluoro-2H-indol-2-one;

(+)-6-chloro-3-[5-chloro-2-(2,2,2-trifluoroethoxy)phenyl]-1,3-dihydro-3-fluoro-2H-indol-2-one;

(±)-3-[5-chloro-2-(2-fluoroethoxy)phenyl]-1,3-dihydro-3-fluoro-6-(trifluoromethyl)-2H-indol-2-one;

(±)-3-[4,5-dichloro-2-(2-fluoroethoxy)phenyl]-1,3-dihydro-3-fluoro-6-(trifluoromethyl)-2H-indol-2-one;

3-[5-chloro-2-(2-fluoroethylthio)phenyl]-1,3-dihydro-3-fluoro-6-(trifluoromethyl)-2H-indol-2-one;

3-[5-chloro-2-(ethylthio)phenyl]-1,3-dihydro-3-fluoro-6-(trifluoromethyl)-2H-indol-2-one;

3-[5-chloro-2-[(2-methylphenylmethyl)thio]phenyl]-1,3-dihydro-3-fluoro-6-(trifluoromethyl)-2H-indol-2-one;

3-[5-chloro-2-(2-methyl-1-propylthio)phenyl]-1,3-dihydro-3-fluoro-6-(trifluoromethyl)-2H-indol-2-one;

3-[5-chloro-2-(1-propylthio)phenyl]-1,3-dihydro-3-fluoro-6-(trifluoromethyl)-2H-indol-2-one;

3-[5-chloro-2-(2,5-difluorophenylmethylthio)phenyl]-1,3-dihydro-3-fluoro-6-(trifluoromethyl)-2H-indol-2-one;

3-[5-chloro-2-(3-chloro-1-propylthio)phenyl]-1,3-dihydro-3-fluoro-6-(trifluoromethyl)-2H-indol-2-one; and (±)-3-[5-chloro-2-(2,2,2-trifluoroethoxy)phenyl]-1,3-dihydro-3-fluoro-6-[4-(trifluoromethyl)phenyl]-2H-indol-2-one.

The general procedures used to synthesize the compounds of Formula I are described in Reaction Schemes 1–4 and are illustrated in the examples. Reasonable variations of the described procedures, which would be evident to one skilled in the art, are intended to be within the scope of the present invention.

REACTION SCHEME 1

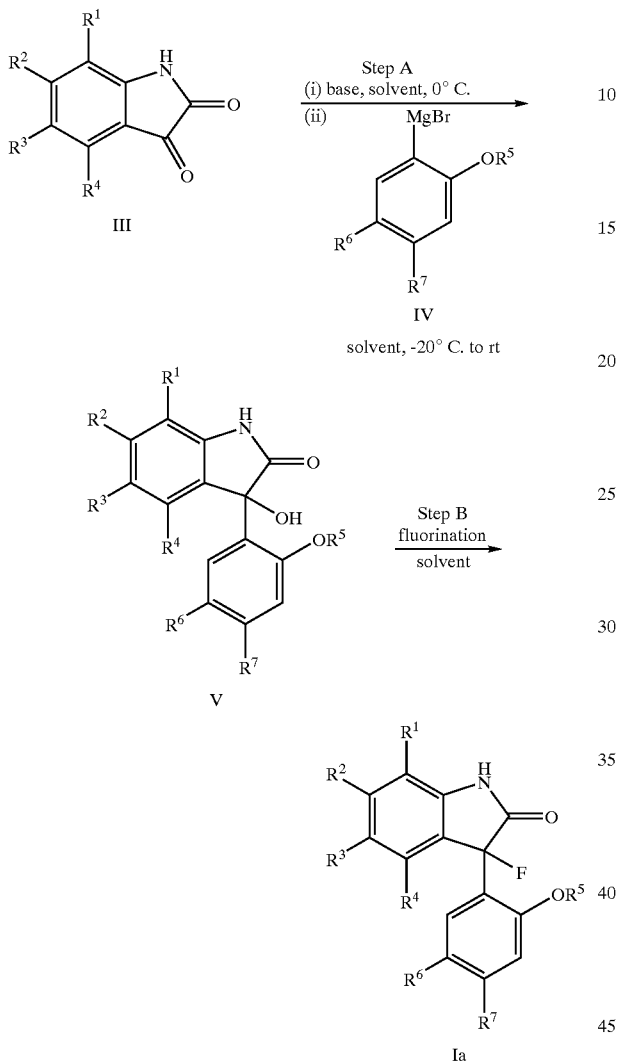

The starting material isatins of Formula III, used in Reaction Scheme 1, were obtained from either commercial sources or prepared by well-known literature procedures such as those described by Hewawasam, P. et al. in U.S. Pat. Nos. 5,565,483 and 5,602,169; Hewawasam, P., et al., *Tetrahedron Lett.*, 1994, 35, 7303; Gassman, P. et al., *J. Org. Chem.*, 1977, 42, 1344; Stolle, R., *J. Prakt. Chem.*, 1922, 105, 137; and Sandmeyer, T., *Helv. Chim. Acta*, 1919, 2, 234. Reaction Scheme 1, Step A, (i) shows the desired substituted isatin of Formula III is first treated with a suitable base in an aprotic solvent at approximately 0° C. in order to generate the corresponding isatin salt. Preferred bases include metal hydride bases, particularly sodium hydride, and a preferred aprotic solvent is THF. The isatin salt is then reacted with an appropriate 2-magnesium bromide aryloxy ether of Formula IV in an appropriate solvent, such as THF within the temperature range of −20° C. to room temperature (rt) to provide the 3-hydroxyoxindoles of Formula V. The 2-magnesium bromide aryloxy ethers (Grignard reagents) of Formula IV used in Reaction Scheme 1, Step A, (ii) were prepared from the corresponding 2-bromo aryloxy ethers (such as Preparations 1–3) according to the procedure as described for Step A of Preparation 4. Reaction Scheme 1, Step B depicts the fluorination of the 3-hydroxyoxindole of Formula V to provide the corresponding 3-fluorooxindole compound of Formula Ia. A preferred method for the fluorination is to treat the 3-hydroxyoxindole of Formula V with diethylaminosulfur trifluoride (DAST) in an aprotic solvent, such as dichloromethane (as described in Example 1) to afford the 3-fluorooxindole of Formula Ia. The substantially pure enantiomeric forms of the 3-fluorooxindoles of Formula Ia may readily be obtained by the separation of the racemic mixture using chiral high pressure liquid chromatography methods as described in Examples 2 and 3.

REACTION SCHEME 2

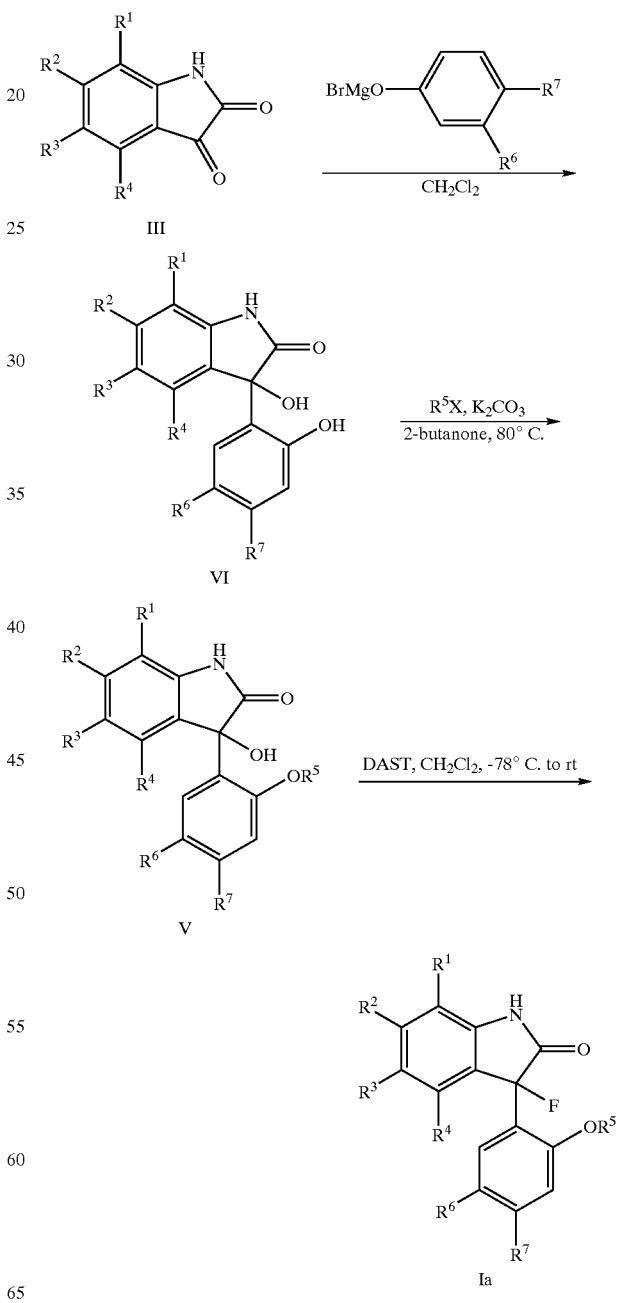

Reaction Scheme 2 depicts the reaction of a magnesium phenolate (prepared by mixing an appropriate phenol and ethyl magnesium bromide) with the desired isatins of Formula III in $CH_2Cl_2$ to afford the desired 3-hydroxyoxindoles of Formula VI (as described in Preparation 5). Selective alkylation of the phenolic hydroxyl moiety of the 3-hydroxyoxindole derivatives of Formula VI is accomplished by treating the compound of Formula VI with $R^5X$ (wherein X is a leaving group such as bromo or iodo) in the presence of a base, such as potassium carbonate, in 2-butanone at approximately 80° C. to afford the 3-hydroxyoxindole ethers of Formula V. The addition of a catalytic amount of an alkali metal halide such as potassium iodide may be desirable in this step (see Preparation 6). Finally, fluorination of the 3-hydroxyoxindole ethers of Formula V with diethylaminosulfur trifluoride (as described in Example 4) provided the desired 3-fluorooxindole derivatives of Formula Ia. The substantially pure enantiomeric forms of the 3-fluorooxindoles of Formula Ia may readily be obtained by the separation of the racemic mixture using chiral high pressure liquid chromatography methods as described in Examples 2 and 3.

Diazotization of the 2-bromoanilines of Formula VII as shown in Reaction Scheme 3, Step (a), is carried out by treatment with sodium nitrite and hydrogen tetrafluroborate in ethanol to provide the diazonium tetrafluoroborate of Formula VIII (as described for the preparation of 2-bromo-4-chlorobenzenediazonium tetrafluoroborate in Preparation 7). Thioalkylation of the 2-bromobenzene diazonium salts of Formula VIII is carried out in Step (b) by treating an acetonitrile solution of the diazonium salt with a sodium thioalkoxide at 0° C. (as described for the preparation of 2-bromo-4-chloro-1-methylthiobenzene in Preparation 8). 2-Bromobenzene disulfides of Formula IX are prepared by treating a hot aqueous solution of potassium ethyl xanthate with the diazonium salt of Formula VIII followed by treatment with potassium hydroxide and ethanol (as described for the preparation of 2-bromo-4-chlorobenzene disulfide in Preparation 9). 2-Bromobenzenethiols of Formula XI are prepared by reduction of the disulfide of Formula IX with sodium borohydride in THF (as described for the preparation of 2-bromo-4-chlorobenzenethiol in Preparation 10). 2-Bromo-1-(tetrahydropyran-2-ylthio)benzene derivatives of Formula XII are prepared from the thiols of Formula XI by treatment with para-toluenesulfonic acid (p-TSA) and 3,4-dihydro-2-H-pyran in $CH_2Cl_2$ as described for the preparation of 2-bromo-4-chloro-1-(tetrahydropyran-2-ylthio)benzene in Preparation 11.

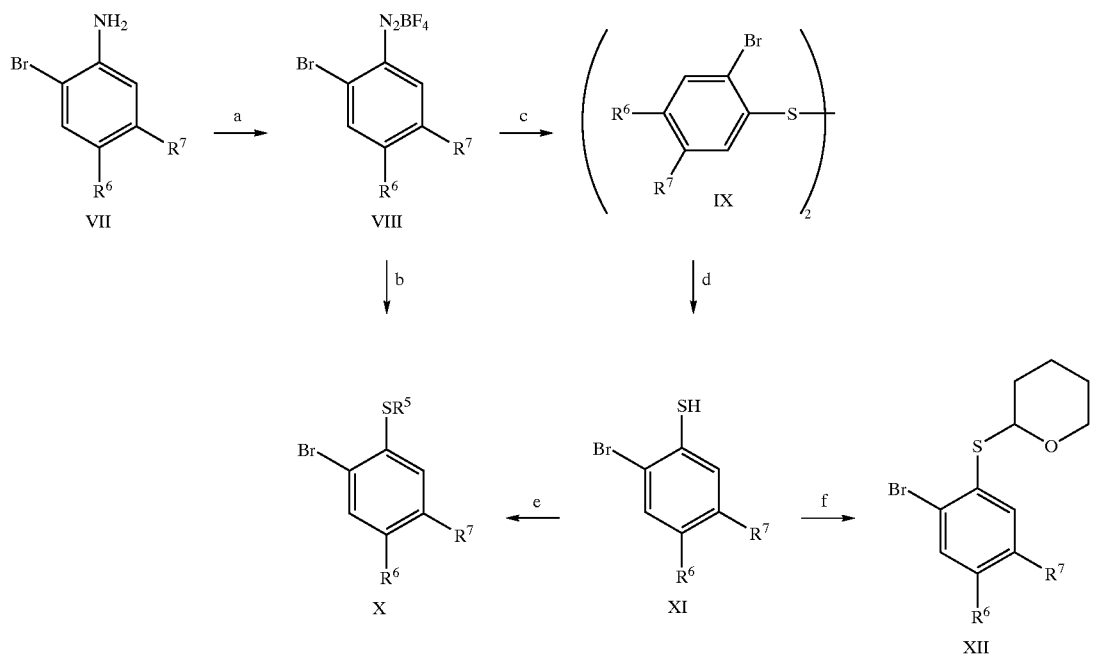

REACTION SCHEME 3 a) $NaNO_2$, $HBF_4$, EtOH
b) $R^5SNa$, $CH_3CN$
c) $EtOS_2K$, $H_2O$
d) $NaBH_4$, THF
e) $R^5X$, $K_2CO_3$, THF
f) 3,4-dihydro-2H-pyran, p-TSA

REACTION SCHEME 4

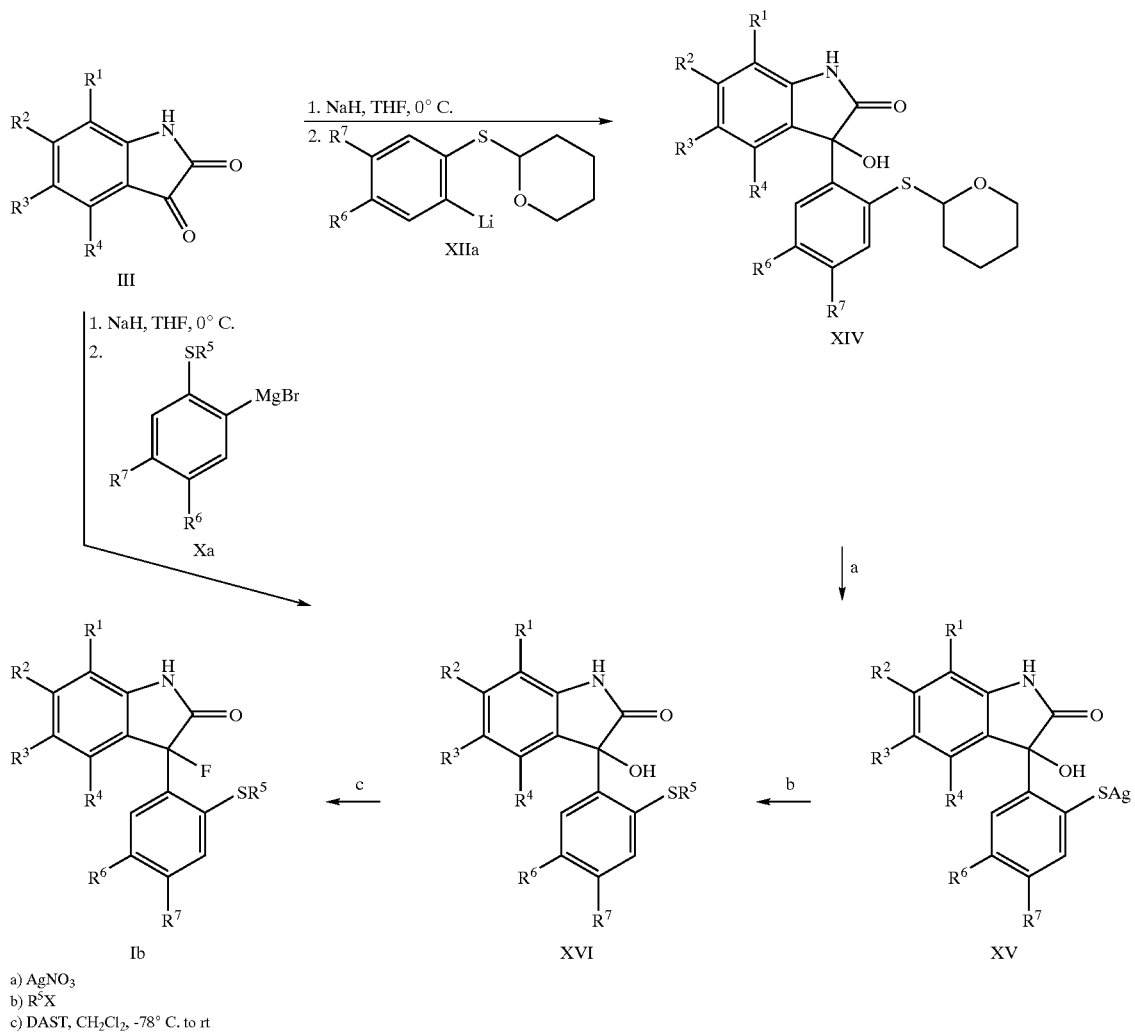

a) AgNO₃
b) R⁵X
c) DAST, CH₂Cl₂, -78° C. to rt

Reaction Scheme 4 depicts the preparation of compounds of Formula Ib. Lithiation of 2-bromo-1-(tetrahydropyran-2-ylthio)benzene derivatives is effected by treatment with a strong base, such as tert-butyllithium in anhydrous THF at approximately −78° C. The resultant aryl lithium intermediate of Formula XIIa is added to the sodium salt of the desired isatin of Formula III (prepared by treatment of isatin with NaH in THF) in THF to provide intermediates of Formula XIV (as described for the preparation of 3-(5-chloro-2-(tetrahydropyran-2-ylthio)phenyl)-3-hydroxy-1H-6-trifluoromethyl-1,3-dihydroindol-2-one in Preparation 12). The intermediate of Formula XIV is then treated with silver nitrate in a polar solvent, such as DMF, to provide the silver salt of Formula XV. The silver salt of the compound of Formula XV is then alkylated by treatment with an appropriate electrophile, R⁵X (e.g. ethyl iodide as used for the synthesis of 3-(5-chloro-2-ethylthiophenyl)-3-hydroxy-1H-6-trifluoromethyl-1,3-dihydroindol-2-one in Preparation 14). Alternatively, hydroxyindolones of Formula XVI can be prepared by addition of a Grignard reagent of Formula Xa to the desired isatins of Formula III as described in Preparation 13. Finally, fluorination of 3-hydroxyindole derivatives of Formula XVI is carried out using diethylaminosulfur trifluoride in an aprotic solvent such as CH₂Cl₂ at approximately −78° C. to provide the fluoro derivatives of Formula Ib (as described in Example 5).

BIOLOGICAL ACTIVITY

KCNQ Oocyte Methods and Results

Potassium (K⁺) channels are structurally and functionally diverse families of K⁺-selective channel proteins which are ubiquitous in cells, indicating their central importance in regulating a number of key cell functions [Rudy, B., *Neuroscience*, 25: 729–749 (1988)]. While widely distributed as a class, K⁺ channels are differentially distributed as individual members of this class or as families. [Gehlert, D. R., et al., *Neuroscience*, 52: 191–205 (1993)]. In general, activation of K⁺ channels in cells, and particularly in excitable cells such as neurons and muscle cells, leads to hyperpolarization of the cell membrane, or in the case of depolarized cells, to repolarization. In addition to acting as an endogenous membrane voltage clamp, K⁺ channels can respond to important cellular events such as changes in the intracellular concentration of ATP or the intracellular concentration of calcium (Ca²⁺). The central role of K⁺ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the KCNQ family exemplified by KCNQ2, KCNQ2/3 heteromultimeres, and KCNQ5, is regulated by transmembrane voltage and plays a potentially important role in the regulation of neuronal excitability [Biervert, C., et al., *Science*, 279: 403–406 (1998); Lerche, C. et al., *J. Biol. Chem.* 275:22395–22400 (2000); Wang, H. et al. *Science*, 282:1890–1893 (1998)].

An opener of KCNQ channels, such as the KCNQ2 and KCNQ2/3 channel opener retigabine, exerts its cellular effects by increasing the open probability of these channels [Main J., *Mol Pharmacol* 58(2):253–62 (2000); Wickenden, A. et al. *Mol. Pharm.* 58:591–600 (2000)]. This increase in the opening of individual KCNQ channels collectively results in the hyperpolarization of cell membranes, particularly in depolarized cells, produced by significant increases in whole-cell KCNQ-mediated conductance.

The ability of compounds described in the present invention to open KCNQ channels and increase whole-cell outward ($K^+$) KCNQ-mediated currents was assessed under voltage-clamp conditions by determining their ability to increase cloned mouse KCNQ2 (mKCNQ2)-mediated, heteromultimeric KCNQ2/3 (m$\mu$KCNQ2/3)-mediated, and human KCNQ5 (hKCNQ5)-mediated outward currents heterologously expressed in Xenopus oocytes. Oocytes were prepared and injected using standard techniques; each oocyte was injected with approximately 50 nl of mKCNQ2, or hKCNQ5 cRNA. In the case of mKCNQ2/3 heteromultimeric channel expression, equal amounts (25–50 nL) of ech cRNA were co-injected. Injection of equivalent amounts of water (50 nl) did not result in expression of outward currents at the voltage steps used to detect KCNQ expression. Following injection, oocytes were maintained at 17° in ND96 medium consisting of (in mM): NaCl, 90; KCl, 1.0; $CaCl_2$, 1:0; $MgCl_2$, 1:0; HEPES, 5.0; pH 7.5. Horse serum (5%) and penicillin/streptomyin (5%) were added to the incubation medium. Recording commenced 2–6 days following mRNA injection. Prior to the start of an experiment oocytes were placed in a recording chamber and incubated in Modified Barth's Solution (MBS) consisting of (in mM): NaCl, 88; $NaHCO_3$, 2.4; KCl, 1.0; HEPES, 10; $MgSO_4$, 0.82; $Ca(NO_3)_2$, 0.33; $CaCl_2$, 0.41; pH 7.5.

Oocytes were impaled with electrodes (1–2 M$\Omega$) and standard 2-electrode voltage clamp techniques were employed to record whole-cell membrane currents. Recordings were accomplished using standard two-electrode voltage clamp techniques [Stuhmer, W., et al., *Methods in Enzymolgy*, Vol. 207: 319–339 (1992)]. Voltage-clamp protocols typically consisted of a series of voltage steps 1–5 sec duration, in +10 mV steps from a holding potential of −90 mV to a maximal potential of +40 mV; records were digitized at 5 kHz and stored on a computer using pClamp data acquisition and analysis software (Axon Instruments). Compounds were evaluated at a single concentration (10 or 20 $\mu$M); the effect of the selected compounds of Formula I on KCNQ2 current was expressed as the percent of control current and is listed in Table I.

TABLE 1

| Example No. | KCNQ2 Current* |
| --- | --- |
| 1 | ++** |
| 2 | ++** |
| 9 | + |

TABLE 1-continued

| Example No. | KCNQ2 Current* |
| --- | --- |
| 10 | + |
| 11 | ++ |
| 12 | ++ |
| 14 | + |

*Unless otherwise noted, at 20 $\mu$M expressed as percent increase over KCNQ current in controls;
**at 10 $\mu$M
+ = 120–150%
++ = >150%

In vivo Electrophysiology

Male Long-Evans rats (Harlan, 250–400 g) were used in the experiments described in this example. Prior to testing, rats were allowed access to food and water ad libitum and were maintained on a 12:12-h light/dark cycle. Rats were group housed in an Association for Assessment and Accreditation of Laboratory Animal Care (AAALAC) accredited facility and cared for in strict compliance with all applicable regulations.

Superior sagital sinus (SSS) stimulation and recording were performed in a manner consistent with previously published methods using cat (Hoskin et al., 1996) and rat (Cumberbatch et al., 1998; 1999) animal models. Rats were anesthetized with 1.2 g/kg i.p. urethane (#U-2500, Sigma Chemical Company, St. Louis, Mo.) and given supplemental urethane as needed. In the case of intravenous (i.v.) drug administration, the jugular veins of the rats were cannulated using sylastic tubing pre-filled with vehicle.

Rats were placed in a stereotaxic device (#1730, David Kopf Instruments, Tujunga, Calif.) and an incision was made to expose the entire skull that continued caudally to the level of the C1/C2 vertebral juncture. Using a microdrill (#770, Dremel, Racine, Wis.) and #4 carbide burr (Henry Schein, Melville, N.Y.), a square section of skull was removed extending from the bregma position, rostrally, to the lambda position, caudally. The underlying dura mater was incised bilateral to the SSS and a small section of Parafilm® (American National Can, Neenah, Wis.) was placed under the SSS to isolate the stimulation electrode. The SSS was stimulated using insulated silver electrodes bent at their ends to form a hook. The dorsal region of the vertebra corresponding to C2 was removed for access to the trigeminal nucleus caudalis.

Stimulated field responses were recorded in the trigeminal nucleus caudalis using Teflon coated stainless-steel microelectrodes (5 megaohms impedance, Frederick Haer, Brunswick, Me.) and amplified and filtered (0.1 Hz–10 kHz) using a differential amplifier (#IsoDAM8, World Precision Instruments, Sarasota, Fla.). Stimulation voltage (250 $\mu$sec, 40–130V) was delivered using a Grass S88 (Grass Medical Instruments, Quincy, Mass.) stimulator and stimulus isolation unit (Grass #SIU5) at a rate of 0.3 Hz. Amplified potentials were captured with an analog-to-digital converter (#1401 plus, Cambridge Electronic Design, Cambridge, UK) and commercially available software (#Signal, Cambridge Electronic Design). Low temperature wax was applied to both the recording and stimulation sites to prevent dehydration.

Three baseline measures (i.e., 100% of control), each consisting of 100 evoked trigeminal field potentials, were sampled prior to drug injection. The primary measure for efficacy were changes in trigeminal field potential amplitude following injection of test compound. A decrease in trigeminal field response amplitude was considered to evidence anti-migraine activity. Following injection of test substances, data were sampled for 1 hour, averaged into 5 minute bins (90 evoked potentials) and expressed as a percent change from average baseline values for the purposes of statistical analysis. Data were analyzed using repeated measures analyses of variance comparing vehicle and drug effects. A difference was considered significant when $p<0.05$.

In one embodiment of the present invention, openers or activators of the KCNQ2 potassium channel protein have been found to be effective in the above-described model of migraine involving vasculo-trigeminal systems which are integrally involved in the transmission of migraine pain. A non-limiting representative compound used in the SSS-stimulated trigeminal model for migraine as described in Example 2 produced a dose-dependent reduction in the SSS-stimulated trigeminal field response (overall ANOVA, $p<0.001$). The compound of Example 2 was prepared as a solution in 100% polyethylene glycol (MW=400) using sonication to aid in dissolution and administered via the i.v. catheter described above at a maximum volume of 0.3 cc. Significant reductions compared with vehicle were observed following the use of doses 0.1, 1.0, 10.0, 30.0 and 50.0 mg/kg i.v., ($p<0.01$ in all cases), with the highest dose (50 mg/kg i.v.) producing a nearly complete blockade of this response (i.e., 86.7±1.67% decrease from control amplitude).

The results of the KCNQ potassium channel openers described above demonstrate that the compounds of the present invention results in the hyperpolarization of cell membranes and for the in vivo SSS-field potential experiments demonstrate that the KCNQ2 openers are useful for modulating neuronal activity and may result in protection from abnormal synchronous firing during a migraine attack. Accordingly, the KCNQ opener or activator compounds described according to the present invention are capable of limiting neuronal activity within the trigeminovascular system and are thus particularly useful for the treatment of migraine headache and migraine attack in individuals suffering from the pain and discomfort of migraine. The compounds of the present invention are therefore useful in the treatment of acutemigraine, as well as the potential for prophylactic treatment of migraine as demonstrated by efficacy in a model of cortical spreading depression. Furthermore, the compounds of the present invention could reduce, ameliorate, eliminate or prevent one, or a number of, the characteristic cluster of symptoms, namely, nausea, photophobia, phonophobia and basic functional disabilities, that are further associated with migraine and migraine pain that occur after the prodrome phase of a migraine headache.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of KCNQ potassium channels in a mammal in need thereof, which comprises administering to said mammal a therapeutically effective amount of a compound of Formula I.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 µg/kg to 10 mg/kg body weight. For parenteral administration, the dose may be in the range of 0.1 µg/kg to 1 mg/kg body weight for intravenous administration. For oral administration, the dose may be in the range of 0.1 µg/kg to 5 mg/kg body weight. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

Preparation of Intermediates

Preparation 1
Preparation of 2-Bromo-4-chloro(2,2,2-trifluoroethoxy) benzene
Step A
Neat methanesulfonyl chloride (28 mL, 0.36 mol) was added dropwise to a stirred cold (0° C.) solution of 2,2,2-trifluoroethanol (30 g, 0.3 mol) and triethylamine (50 mL, 0.36 mol) in $CH_2Cl_2$ (60 mL). The reaction mixture was allowed to warm to ambient temperature and maintained at room temperature for 1–2 hours. The reaction mixture was quenched with 1N HCl (50 mL) and the organic layer was separated and then washed consecutively with water and brine. The organic layer was dried over $MgSO_4$, filtered and the filtrate was concentrated in vacuo to afford a colorless oil which was distilled under reduced pressure to afford 2,2,2-trifluoroethylmethane sulfonate (51.8g; 98%): bp 100–105° C. @ 25–30 torr.
Step B
To a stirred cold (0° C.) suspension of oil free NaH (0.12 mol, 4.8 g of 60% NaH in mineral oil) in anhydrous DMF (50 mL), a solution of 2-bromo-4-chlorophenol in DMF (50 mL) was added over 30 minutes under nitrogen. The resultant gray suspension of the sodium salt of 2-bromo-4-chlorophenol was treated with neat 2,2,2-trifluoroethylmethane sulfonate (21.4 g, 0.12 mol). The stirred mixture was heated at reflux temperature for 2–3 days. The mixture was cooled in an ice water bath and extracted with diethyl ether (2×100 mL). The combined ether extract was washed with 1N NaOH (3×100 mL), 1N HCl, brine, dried over $Na_2SO_4$, and filtered. The filtrate was concentrated in vacuo to provide a golden-yellow oil (18.4 g) which was then distilled in vacuo to afford the title compound as a colorless oil (14.7 g): bp 100–103° C. @ 0.5 torr.

Preparation 2
Preparation of 2-Bromo4-chloro(2,2-difluoroethoxy) benzene
A stirred suspension of 2-bromo-4-chlorophenol (2.07 g, 10 mmol), 2-bromo-1,1-difluoroethane (1.74 g, 12 mmol) and potassium carbonate (1.65 g, 12 mmol) in 2-butanone (10 mL) was heated at reflux temperature for 16 hours. The suspension was allowed to cool and then filtered. The filtrate was concentrated and distilled in vacuo to afford the title compound as a colorless oil (2.28 g, 84%): bp 78–80° C. @ 0.1 torr Preparation 3
Preparation of 2-Bromo-4-chloro(2-fluoroethoxy)benzene
A stirred suspension of 2-bromo-4-chlorophenol (2.07 g, 10 mmol), 1-bromo-2-fluoroethane (1.52 g, 12 mmol) and potassium carbonate (1.65 g, 12 mmol) in 2-butanone (10 mL) was heated at reflux temperature for 16 hours. The suspension was allowed to cool and then filtered. The filtrate was concentrated in vacuo and then distilled in vacuo to afford the titled compound as a colorless oil (2.25 g, 89%): bp 80–82° C. @ 0.1 torr Preparation 4
Preparation of (±)-3-[5-Chloro-2-[(2,2,2-trifluoroethoxy) phenyl]-1,3-dihydro-3-hydroxy-6-(trifluoromethyl)-2H-indol-2-one
Step A
To a stirred suspension of magnesium turnings in dry THF (30 mL), was added dibromoethane (0.77 mL) under nitrogen and allowed to react for 10–15 minutes. Neat 2-bromo-4-chloro(2,2,2-trifluoroethoxy)benzene (13.0 g, 45 mmol) was then added. Once the ensuing exothermic reaction had subsided the reaction mixture was heated to reflux for 2–3 hours then was allowed to cool to room temperature.
Step B
In a separate flask, neat 6-(trifluoromethyl)isatin (6.45 g, 30 mmol) was added to a cold (0° C.) suspension of oil free NaH (60% in oil, 1.44 g, 36 mmol) in dry THF (30 mL) under nitrogen. The mixture was stirred until gas evolution ceased. The sodium salt of the 6-(trifluoromethyl)isatin was cooled to −20° C. and then the Grignard reagent 2-(magnesium bromide)-4-chloro(2,2,2-trifluoroethoxy) benzene (from Step A, above) was added via syringe. The reaction mixture was allowed to warm to room temperature and maintained at room temperature for 30 minutes. The reaction mixture was diluted with diethyl ether and then quenched with 1N HCl. The organic layer was separated and washed consecutively with 0.5N NaOH (2×50 mL), 1N HCl, water, brine and then dried over $Na_2SO_4$ and filtered. The filtrate was concentrated in vacuo to provide a light brown solid (16.3 g) which was triturated with $CH_2Cl_2$ to afford the titled compound (8.92 g, 70%) as a white solid: mp 226–228° C.

Preparation 5

Preparation of (±)-3-(5-chloro-2-hydroxyphenyl)-1,3-dihydro-3-hydroxy-6-(trifluoromethyl)-2H-indole-2-one To a solution of 4-chlorophenol (2.87 g, 22.3 mmol) in THF (30 mL) at 0° C., 1.0 M solution of ethyl magnesium bromide (22.3 mL, 22.3 mmol) in THF was added dropwise. The resulting white suspension was then concentrated to dryness and dissolved in $CH_2Cl_2$ (30 mL). Neat 6-(trifluoromethyl)isatin (4.0 g, 18.6 mmol) was then added at once. After stirring at room temperature for 4 hours, the reaction was quenched with 1N HCl solution. The organic layer was separated, washed with water and brine, dried over $MgSO_4$, and filtered. The filtrate was concentrated in vacuo to provide a dark red oil which was purified by flash column chromatography (silica gel, 1:1 hexanes/EtOAc) to afford the title compound as an orange solid (5.48 g, 86% yield). $^1H$ NMR (DMSO-$d_6$): δ10.61 (s, 1H), 9.73 (s, 1H), 7.73(d, J=2.7 Hz, 1H), 7.15–7.21 (m, 2H), 7.03–7.07 (m, 2H), 6.81 (s, 1H), 6.61 (d, J=8.6 Hz, 1H).

Preparation 6
Preparation of (±)-3-[5-chloro-2-[4-(trifluoromethyl) phenylmethoxy]phenyl]-1,3-dihydro-3-hydroxy-6-(trifluoromethyl)-2H-indole-2-one
To a solution of (±)-3-(5-chloro-2-hydroxyphenyl)-1,3-dihydro-3-hydroxy-6-(trifluoromethyl)-2H-indole-2-one (Preparation 5, 80 mg, 0.233 mmol) in 2-butanone (3mL), was added 4-(trifluoromethyl) benzyl bromide (61 mg, 0.256 mmol), $K_2CO_3$ (32 mg, 0.233 mmol) and a catalytic amount of KI. The reaction mixture was heated at 75–80° C. for 2 days. The reaction mixture was then filtered and the filtrate was concentrated in vacuo. The resulting crude product was purified by preparative HPLC to afford the title compound (70 mg, 60% yield); MS m/e 500 (M–H)⁻.

Preparation 7
Preparation of 2-bromo-4-chlorobenzenediazonium tetrafluoroborate
A solution of 2-bromo-4-chloroaniline (10.0 g, 48.4 mmol) and $HBF_4$ in EtOH (60 mL) kept at 0° C. was treated with an aqueous solution (20 mL) of $NaNO_2$ (3.34g, 48.4 mmol). After completion of the addition, diethyl ether (200 mL) was added to the mixture. The solid was collected by filtration, washed with water and dried under high vacuum affording the title compound (14.2 g, 96%) as white crystals.

Preparation 8
Preparation of 2-bromo-4-chloro-1-methylthiobenzene
A cold (0° C.) solution of 2-bromo-4-chlorobenzenediazonium tetrafluoroborate (5.0 g, 16.3 mmol) in $CH_3CN$ (50 mL) was treated portion wise with sodium thiomethoxide (1.15 g, 16.4 mmol) and a strong evolution of gas ($N_2$) was observed. The mixture was warmed up to 23° C., stirred for 0.25 hours and filtered. The filtrate was concentrated in vacuo; the residue was taken up in $CH_2Cl_2$, stirred and the solution was then filtered. The $CH_2Cl_2$ filtrate was concentrated in vacuo affording a brown syrup that was distilled under vacuum to provide the purified title compound; bp 125° C./0.4 mm, 1.4 g, 37%. $^1$H NMR ($CDCl_3$) δ7.56 (d, J=2.5 Hz, H-3, 1H), 7.30 (dd, J=2.5 Hz, J=8.6 Hz, H-5, 1H), 7.07 (d, J=8.6 Hz, H-6, 1H), 2.49 (s, $CH_3$, 3H). IR 1569, 1544, 1450, 1434, 1371,1248, 1105, 1024, 868, 803, 784 cm$^{-1}$. Anal. Calcd. for $C_7H_6BrClS$: C, 35.39; H, 2.55. Found: C, 34.89; H, 2.51.

Preparation 9
Preparation of 2-bromo-4-chlorobenzene disulfide
To a hot aqueous solution (70° C., 100 mL) of potassium ethyl xanthate (13.5 g, 84.2 mmol) was carefully added an aqueous suspension (50 mL) of 2-bromo-4-chlorobenzenediazonium tetrafluoroborate (13 g, 42.4 mmol). After the addition was completed, the mixture was stirred at 70° C. for 1 hour and, treated successively with KOH (12.5N, 20 mL) and EtOH (40 mL). The mixture was stirred at 80° C. for 16 hours and after cooling to 23° C. was acidified with concentrated HCl and extracted with diethyl ether. The organic layer was dried over $MgSO_4$, filtered and the filtrate was concentrated in vacuo. The crude material was purified by chromatography on a silica gel column with a mixture of 20% EtOAc/hexane as eluting solvent to afford 8.6 g of the title compound. Trituration in MeOH provided an analytical sample; mp 75–78° C.; $^1$H NMR ($CDCl_3$) δ7.65–7.55 (m, 2H), 7.46 (d, J=8.5 Hz, 2H), 7.35–7.2 (m, 2H);IR 1558, 1540, 1446. 1437, 1097, 1018, 806, 777 cm$^{-1}$.

Preparation 10
Preparation of 2-bromo-4-chlorobenzenethiol
A solution of 2-bromo-4-chlorobenzene disulfide (3.8 g, 8.5 mmol) in THF (30 mL) was treated with $NaBH_4$ (0.83 g, 22.0 mmol). The mixture was refluxed for a while and treated with MeOH (2 mL); heating was resumed for 0.5 hours. Mixture was cooled to 23° C., acidified with HCl (3N) and extracted with $Et_2O$. The $Et_2O$ extracts were dried over $MgSO_4$, filtered, and the filtrate was concentrated in vacuo to afford the title compound which was used without further purification.

Preparation 11
Preparation of 2-bromo4-chloro-1-(tetrahydropyran-2-ylthio)benzene
A mixture of 2-bromo-4-chlorothiophenol (3.74 g, 16.8 mmol), p-toluene sulfonic acid (0.427 g, 1.7 mmol) and 3,4-dihydro-2-H-pyran (0.985 ml, 16.8 mmol) in $CH_2Cl_2$ (30 mL) was stirred at 23° C. for 18 hours. After the addition of NaOH, the organic phase was separated, dried over $MgSO_4$, filtered and the filtrate was concentrated in vacuo to afford the title compound as a yellow oil, (4.91 g, 95%) $^1$H NMR ($CDCl_3$) δ7.6–7.5 (m, 2H), 7.35–7.2 (m, 1H), 5.37 (t, J=4.5 Hz, SCHO, 1H), 4.25–4.1 (m, $CH_2O$, 1H), 3.7–3.55 (m, $CH_2O$, 1H), 2.2–2.05 (m, 1H), 2.0–1.8 (m, 2H), 1.8–1.6 (m, 3H): IR 1566, 1542, 1450, 1367, 1257, 1188, 1101, 1037, 1024, 1008, 867, 809, 783 cm$^{-1}$; Anal. Calcd. for $C_{11}H_{12}BrClOS$: C, 42.95; H, 3.93. Found: C,43.15; H, 3.91.

Preparation 12
Preparation of 3-(5-chloro-2-(tetrahydropyran-2-ylthio)phenyl)-3-hydroxy-1 H-6-trifluoromethyl-1,3-dihydroindol-2-one:
A cold (−78° C.) solution of 2-bromo4-chloro-1-(tetrahydropyran-2-ylthio)benzene (1.5 g, 4.87 mmol) in dry THF (10 mL) under an argon atmosphere was treated with tert-BuLi (1.7 M, 6.3 mL, 10.7 mmol) and stirred for 0.5 hours. The resulting solution was added to a solution (23° C.) of 6-trifluoromethyl-1-H-indole-2,3-dione sodium salt (generated by addition of NaH to a cold (−15° C.) solution of 6-trifluoromethyl-1-H-indole-2,3-dione in dry THF (15 mL) that was stirred for 0.25 hours). The mixture was quenched by addition of an aqueous saturated solution of $NH_4Cl$ and diluted with $Et_2O$. The organic layer was separated, dried over $MgSO_4$, filtered and the filtrate was concentrated in vacuo to afford a residue (2.16 g, 100%). The residue was triturated with a $CH_2Cl_2$/hexane mixture to afford the purified title compound; $^1$H NMR (DMSO-d6) δ10.84 and 10.82–(2s, 1H), 8.03 and 8.00 (2s, 1H), 7.5–7.4 (m, 2H), 7.3–7.2 (m, 1H), 7.15–6.95 (m, 2H), 5.0–4.9 (m, SCHO, 1H), 3.95–3.8 (m, $OCH_2$, 1H), 3.7–3.5 (m, 1H), 3.45–3.3 (m, $OCH_2$, 1H), 1,9–0.9 (m, 6H); IR 1718, 1637, 1458, 1319, 1167, 1134, 1116, 1057, 1036, 1009 cm$^{-1}$; Anal. Calcd. for $C_{20}H_{17}ClF_3NO_3S$: C, 54.12; H, 3.86; N, 3.16. Found: C, 54.05; H, 3.62; N, 3.16; High Resolution Mass Spectrum (HRMS)/ESI $C_{20}H_{16}O_3F_3N^{35}ClS$ (M−H)⁻; 442.049153 found: 442.04978.

Preparation 13
Preparation of 3-(5-chloro-2-(2-methylprop-2-ylthio)phenyl)-3-hydroxy-1H-6-trifluoromethyl-1,3-dihydroindol-2-one
A mixture of 2-bromo-4-chloro-1-(2-methylprop-2-ylthio)benzene (0.90 g, 3.3 mmol) and magnesium turnings (0.10 g, 4.0 mmol) in dry THF (5 mL) was heated gently to initiate the reaction and then stirred at 23° C. for 0.75 hours. The resultant brown slurry was added to a solution (23° C.) of the 6-trifluoromethyl-1-H-indole-2,3-dione sodium salt in dry THF (10 mL) (generated from isatin (0.43g, 2.0 mmol) and NaH (0.063 g, 2,6 mmol) at 0° C.). The mixture was warmed up to 23° C. and stirred for 1 hour. After quenching the reaction with saturated aqueous $NH_4Cl$ solution, the mixture was extracted with $Et_2O$. The $Et_2O$ extracts were concentrated in vacuo and the residue was purified by silica gel column chromatography to afford the title compound: $^1$H NMR (DMSO-d6) δ10.79 (s, NH, 1H), 8.04 (s, 1H), 7.5–7.4 (m, 2H), 7.21 (d, J=8.1 Hz, 1H), 7.08 (s, 1H), 7.02 (d, J=6.6 Hz, 1H), 7.01 (s, 1H), 0.97 (s, S-tBu, 9H); IR 1720, 1637, 1460, 1319, 1169, 1134, 1122, 1057 cm$^{-1}$; HRMS/ESI $C_{19}H_{17}O_2NF_3$ $^{35}ClS$ (M−H)⁻; 414.054161 found: 414.054161

Preparation 14

Preparation of 3-(5-chloro-2-ethylthiophenyl)-3-hydroxy-1H-6-trifluoromethyl-1,3-dihydroindol-2-one A solution of 3-(5-chloro-2-(tetrahydropyran-2-ylthio)phenyl)-3-hydroxy-1H-6-trifluoromethyl-1,3-dihydroindol-2-one (0.153 g, 0.344 mmol) in DMF (2 mL) was first treated with an aqueous solution of $AgNO_3$ (0.5M, 0.69 ml), stirred at 23° C. for 0.25 hours and then treated with ethyl iodide (55 μl, 0.688 mmol). The mixture was stirred at 80° C. for 2 hours, and was then treated with HCl (3N) after cooling to 23° C. The reaction mixture was then filtered on a Celite pad. The filter cake was washed with $CH_3OH$. The filtrate and washings were combined and concentrated in vacuo. The residue was dissolved in EtOAc and the solution washed with $H_2O$ and brine. The organic layer was dried over $MgSO_4$, filtered and the filtrate concentrated in vacuo. The crude material was purified by silica gel column chromatography to afford the title compound (0.53 g, 40%) as white crystals; mp 167–169° C.; $^1H$ NMR (DMSO-$d_6$) δ10.81 (s, NH, 1H), 8.0 (d, J=2.0 Hz, 1H), 7.5–7.2 (m, 2H), 7.23 (d, J=8.6 Hz, 1H), 7.08 (d, J=6.0 Hz, 1H) , 7.01 (d, J=8.1 Hz, 1H), 2.7–2.6 (m, $SCH_2$, 1H,), 2.6–2.45 (m, $SCH_2$ partially masked by DMSO, 1H), 0.83 (t, J=7 Hz, $CH_3$, 3H); IR 1716, 1635, 1458, 1317, 1173, 1130, 1057 $cm^{31\ 1}$; Anal. Calcd. for $C_{17}H_{13}ClF_3NO_2S$: C, 52.65; H, 3.38; N, 3.61. Found: C, 52.29; H, 3.10; N, 3,60; HRMS/ESI $C_{17}H_{12}O_2F_3N^{35}ClS$ (M–H)$^-$; 387.02295 found: 386.02097.

The following examples illustrate the preparation of the compounds of Formula I by following the general procedures described herein.

EXAMPLE 1

(±)-3-[5-Chloro-2-[(2,2,2-trifluoroethoxy)phenyl]-1,3-dihydro-3-fluoro-6-(trifluoromethyl)-2H-indol-2-one Neat diethylaminosulfur trifluoride (3.66 mL, 0.03 mol) was added dropwise to a cold (−78° C.) stirred partial solution of (±)-3-[5-chloro-2-[(2,2,2-trifluoroethoxy)phenyl]-1,3-dihydro-3-hydroxy-6-(trifluoromethyl)-2H-indol-2-one (Preparation 4, 6.4 g, 0.015 mol) in anhydrous $CH_2Cl_2$ (45 mL) under a nitrogen atmosphere. The resultant mixture was allowed to warm in an ice-bath and maintained at 0° C. After 1 hour, TLC showed absence of starting material. The reaction mixture was quenched with slow addition of cold water (20–25 mL) at 0° C. The organic layer was separated, washed with water (30 mL), brine (30 mL) and then dried over $MgSO_4$ and filtered. The filtrate was concentrated in vacuo to give the crude product (6.9 g). The crude product was purified by recrystallization from $CH_2Cl_2$/ether/hexanes to provide the titled compound as an off-white crystalline solid (5.94 g, 93%): mp 208–210° C.; $^1H$ NMR (DMSO-$d_6$): δ4.50–4.65 (m, 2H), 7.12 (m, 2H), 7.30–7.35 (m, 2H), 7.56 (dd, 1H, J=5.3 and 1.6 Hz), 7.72 (d, 1H, J=1.4 Hz), 11.20 (s, 1H).

Anal. Calcd. for $Cl_7H_9ClF_7NO_2$: C, 47.74; H, 2.12, N, 3.27. Found: C, 47.63; H, 2.18, N, 3.21.

EXAMPLE 2

Isolation of (±)-3-[5-Chloro-2-[(2,2,2-trifluoroethoxy)phenyl]-1,3-dihydro-3-fluoro-6-(trifluoromethyl)-2H-indol-2-one The racemic compound (±)-3-[5-chloro-2-[(2,2,2-trifluoroethoxy)phenyl]-1,3-dihydro-3-fluoro-6-(trifluoromethyl)-2H-indol-2-one obtained in Example 1 was separated into its enantiomers using a Chiracel-OD analytical HPLC column (250×4 mm) using 9:1 hexanes/isopropyl alcohol as the eluting solvent at a flow rate of 0.7 mL/min. The detection method employed a HP 1090 UV detector with diode array at a wavelength of 220 nm. The first enantiomer which eluted from the column had a retention time of about 8.64 minutes and was determined to be the (+)-enantiomer of the title compound. On a preparative scale, up to two grams of the racemate may be resolved with a single injection on a 5×50 cm Chiracel-OD preparative HPLC column using 9:1 hexanes/isopropyl alcohol at a flow rate of 60 mL/min with baseline separation. The (+)-enantiomer was identical to the racemate with respect to NMR, mass spectra, TLC and IR. The title compound was found to have a mp=68–69° C. and $[\alpha]_D^{25}$+120.50° ($CHCl_3$).

EXAMPLE 3

Isolation of (−)-3-[5-Chloro-2-[(2,2,2-trifluoroethoxy)phenyl]-1,3-dihydro-3-fluoro-6-(trifluoromethyl)-2H-indol-2one Using the same isolation process as described above for Example 2, the second enantiomer eluted from the same column at a retention time of about 15.19 minutes was determined to be the (−)-enantiomer of the title compound. The (−)-enantiomer was identical to the racemate with respect to NMR, mass spectra, TLC and IR. The title compound was found to have a mp=69–70° C. and $[\alpha]_D^{25}$−128.1° ($CHCl_3$).

EXAMPLE 4

Preparation of (±)-3-[5chloro-2-[4-(trifluoromethyl)phenylmethoxy]phenyl]-1,3-dihydro-3-fluoro-6-(trifluoromethyl)-2H-indole-2-one To a suspension of (±)-3-[5-chloro-2-[4-(trifluoromethyl)phenyl-methoxy]phenyl]-1,3-dihydro-3-hydroxy-6-(trifluoromethyl)-2H-indole-2-one (Preparation 6, 45 mg, 0.09 mmol) in $CH_2Cl_2$ (3 mL), was added dropwise neat diethylaminosulfur trifluoride (0.018 mL, 0.135 mmol) at −78° C. The reaction mixture was warmed to room temperature for 15 minutes and then quenched with water. The organic layer was separated, washed with water, dried over $MgSO_4$ and filtered. The filtrate was concentrated in vacuo to provide the title compound (35 mg, 77% yield). MS m/e 502 (MH$^-$). $^1H$ NMR ($CDCl_3$): δ7.84 (d, J=1.95 Hz, 1H), 7.68 (s, 1H), 7.53 (d, J=8.1 Hz, 2H), 7.36 (dd, J=8.7 Hz, 2.5 Hz, 1H), 7.29 (m, 1H), 7.21 (m, 1H), 7.05 (d, J=8.1 Hz, 2H), 6.81(dd, J=8.8 Hz, 1.1 Hz, 1H), 6.73 (s, 1H), 4,88 (d, 11.0 Hz, 1H), 4.73 (d, J=11.0 Hz,1H).

EXAMPLE 5

Preparation of 3-(5-chloro-2-methylthiophenyl)-3-fluoro-1H-6-trifluoromethyl-1,3-dihydroindol-2-one A solution of 3-(5-chloro-2-methylthiophenyl)-3-hydroxy-1H-6-trifluoromethyl-1,3-dihydroindol-2-one (0.28 g, 0.75 mmol) in $CH_2Cl_2$ (12 mL) was cooled at −78° C. and treated with diethylaminosulfur trifluoride (0.130 mL, 0.97 mmol). After removing the cooling bath, the mixture was stirred at 23° C. for 0.25 hours and quenched by the addition of water. The two phases were separated and the aqueous phase was extracted with EtOAc. The combined organic layers were dried over $MgSO_4$, filtered and the filtrate was concentrated in vacuo. The residue was purified by column chromatography on silica gel. Trituration of the pure product with a $CH_2Cl_2$/hexane mixture afforded the title compound (0.243 g, 86%), as a crystalline solid.

mp157–158° C.; $^1$H NMR (DMSO-d$_6$) δ11.37 (s, NH, 1H), 7.75 (s, 1H), 7.57 (dd, J=2.5 Hz, J=8.6 Hz, 1H), 7.53 (d, J=8.6 Hz, 1H), 7.4–7.3 (m, 2H), 7.2 (s, 1H), 2.22 (s, SCH$_3$, 3H); IR 1728, 1637,1458, 1318, 1235, 1174, 1130, 1058 cm$^-$;

Anal. Calcd. for C$_{16}$H$_{10}$ClF$_4$NOS: C, 51.14; H, 2.68; N, 3.73. Found: C, 51.08; H, 2.38; N, 3,53;

HRMS/MAB C$_{16}$H$_9$O$_3$F$_4$N$^{35}$ClS (M$^+$); 375.01077 found: 375.0097.

Procedure for Examples 6–13

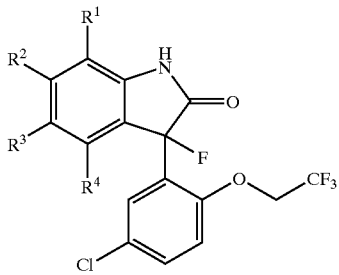

Examples 6–11 were prepared by reacting the Grignard reagent derived from 2-bromo-4-chloro(2,2,2-trifluoroethoxy)benzene (Preparation 1) and an appropriately substituted 2,3-indolinedione according to the methods described previously for Preparation 4. The resulting intermediate (±)-3-[5-chloro-2-[(2,2,2-trifluoroethoxy)phenyl]-1,3-dihydro-3-hydroxy-2H-indol-2-one derivative was then fluorinated using diethylaminosulfur trifluoride according to the method as described for Example 1 to provide the compounds of Examples 6–11. Examples 12 and 13 were obtained from Example 11 by separation of the enantiomers according to the methods as previously described for Examples 2 and 3.

EXAMPLE 6

(±)-3-[5-Chloro-2-(2,2,2-trifluoroethoxy)phenyl]-1,3-dihydro-3,6-difluoro-2H-indol-2-one; (R$^1$, R$^3$, R$^4$ are H; R$^2$ is F)

mp 200–202° C.; MS m/e 376 (M–H)$^-$

EXAMPLE 7

(±)-3-[5-Chloro-2-(2,2,2-trifluoroethoxy)phenyl]-1,3-dihydro-3-fluoro-6-(fluoromethyl)-2H-indol-2-one; (R$^1$, R$^3$, R$^4$ are H; R$^2$ is CH$_2$F)

mp 150–151° C.; MS m/e 390 (M–H)$^-$.

EXAMPLE 8

(±)-3-[5-Chloro-2-(2,2,2-trifluoroethoxy)phenyl]4,6-dichloro-1,3-dihydro-3-fluoro-2H-indol-2-one; (R$^1$ and R$^4$ are H; R$^2$ and R$^3$ are Cl)

mp 230–232° C.; MS m/e 427 (M–H)$^-$.

EXAMPLE 9

(±)-3-[5-Chloro-2-(2,2,2-trifluoroethoxy)phenyl]-5,6-dichloro-1,3-dihydro-3-fluoro-2H-indol-2-one; (R$^1$ and R$^3$ are H; R$^2$ and R$^4$ are Cl)

mp 200–202° C.; MS m/e 427 (M–H)$^-$.

EXAMPLE 10

(±)-3-[5-Chloro-2-(2,2,2-trifluoroethoxy)phenyl]-1,3-dihydro-3,5,6-trifluoro-2H-indol-2-one; (R$^1$ and R$^3$ are H, R$^2$ and R$^4$ are F)

mp 200–203° C.; MS m/e 394 (M–H)$^-$.

EXAMPLE 11

(±)-6-Chloro-3-[5-chloro-2-(2,2,2-trifluoroethoxy)phenyl]-1,3-dihydro-3-fluoro-2H-indol-2-one; (R$^1$, R$^3$, R$^4$ are H; R$^2$ is Cl)

mp 167–169° C.; MS m/e 393 (M–H)$^-$.

EXAMPLE 12

(+)-6-Chloro-3-[5-chloro-2-(2,2,2-trifluoroethox)phenyl]-1,3-dihydro-3-fluoro-2H-indol-2-one; (R$^1$, R$^3$, R$^4$ are H; R$^2$ is Cl)

$[α]_D^{25}$+149.30 (CHCl$_3$); MS m/e 393 (M–H)$^-$.

EXAMPLE 13

(−)-6-Chloro-3-[5chloro-2-(2,2,2-trifluoroethoxy)phenyl]-1,3-dihydro-3-fluoro-2H-indol-2-one; (R$^1$, R$^3$, R$^4$ are H; R$^2$ is Cl)

$[α]_D^{25}$−146.3° (CHCl$_3$); MS m/e 393 (M–H)$^-$.

Procedure for Examples 14–15

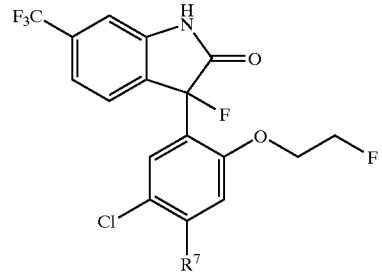

Examples 14 and 15 were prepared by reacting the Grignard reagent derived from either 2-bromo-4-chloro(2-fluoroethoxy)benzene (Preparation 3, for Example 14) or 2-bromo-4,5-dichloro(2-fluoroethoxy)benzene (for Example 15), respectively, and the sodium salt of 6-trifluoromethyl 2,3-indolinedione according to the methods described previously for Preparation 4. The resulting intermediate (±)-3-[5-chloro-2-[(2-fluoroethoxy)phenyl]-1,3-dihydro-3-hydroxy-2H-indol-2-one (for Example 14) or (±)-3-[4,5-dichloro-2-[(2-fluoroethoxy)phenyl]-1,3-dihydro-3-hydroxy-2H-indol-2-one (for Example 15) was then fluorinated using diethylaminosulfur trifluoride according to the method as described for Example 1 to provide the title compounds of Examples 14 and 15, respectively.

EXAMPLE 14

(±)-3-[5-Chloro-2-(2-fluoroethoxy)phenyl]-1,3-dihydro-3-fluoro-6-(trifluoromethyl)-2H-indol-2-one; (R$^7$ is H)

MS m/e 390 (M–H$^-$); $^1$H-NMR (CDCl$_3$, δ=ppm) 7.83 (d, J=1.9 Hz, 1H), 7.66 (brd s, 1H), 7.50 (dd, J=8.7,2.4 Hz, 1H), 7.33–7.19 (m, 2H), 7.16 (s, 1H), 6.73 (d, J=7.5 Hz, 1H), 4.68–3.85 (m, 4H).

EXAMPLE 15

(±)-3-[4,5-Dichloro-2-(2-fluoroethoxy)phenyl]-1,3-dihydro-3-fluoro-6-(trifluoromethyl)-2H-indol-2-one; ($R^7$ is Cl)

MS m/e 448 (M+Na)$^+$.

Procedure for Examples 16–22

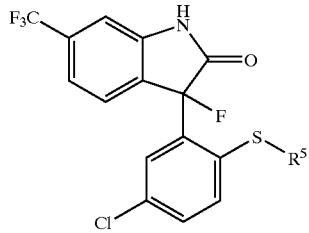

Examples 16–22 were prepared by fluorination of the 3-hydroxy moiety of the corresponding 3-[5-chloro-2-(alkylthio)phenyl]-1,3-dihydro-3-hydroxy-6-(trifluoromethyl)-2H-indol-2-one with diethylaminosulfur trifluoride according to the procedure as previously described in Example 5. The 3-[5-chloro-2-(alkylthio)phenyl]-1,3-dihydro-3-fluoro-6-(trifluoromethyl)-2H-indol-2-one was then isolated as in Example 5 to provide the title compounds of Examples 16–22. The 3-[5-chloro-2-(alkylthio)phenyl]-1,3-dihydro-3-hydroxy-6-(trifluoromethyl)-2H-indol-2-one intermediates were prepared by alkylation of the silver salt of the thiol (described in Preparation 14) with an appropriate electrophile according to the procedure previously described for Preparation 14. For example, 3-[5-chloro-2-(2-fluoroethylthio)phenyl]-1,3-dihydro-3-fluoro-6-(trifluoromethyl)-2H-indol-2-one (compound of Example 16) was prepared by alkylation of the thiol silver salt (of Preparation 14) with 1-bromo-2-fluoroethane followed by fluorination with diethylaminosulfur trifluoride.

EXAMPLE 16

3-[5-Chloro-2-(2-fluoroethylthio)phenyl]-1,3-dihydro-3-fluoro-6-(trifluoromethyl)-2H-indol-2-one; ($R^5$ is $CH_2CH_2F$)

$^1$H NMR (DMSO-$d_6$) δ11.35 (s, NH, 1H), 7.79 (s, 1H), 7.68 (d, J=9.6 Hz, 1H), 7.6 (dd, J=2.5 Hz, J=8.6 Hz, 1H), 7.3-7.3 (m, 2H), 7.21 (s, 1H), 4.35–4.1 (2m, $CH_2F$, 2H), 3.15–2.8 (m, $SCH_2$, 2H); IR 1734, 1635, 1458, 1319, 1236, 1170, 1130, 1057 cm$^-$; HRMS/ESI $C_{17}H_{10}OF_5N^{35}ClS$ (M–H)$^-$; 406.009176 found: 406.0098.

EXAMPLE 17

3-[5-Chloro-2-(ethylthio)phenyl]-1,3-dihydro-3-fluoro-6-(trifluoromethyl)-2H-indol-2-one; ($R^5$ is $CH_2CH_3$)

mp 105–7° C.; $^1$H NMR (DMSO-$d_6$) δ11.36 (s, NH, 1H), 7.78 (s, 1H), 7.65–7.5 (m, 2H), 7.4–7.25 (m, 2H), 7.2 (s, 1H), 2.8–2.55 (2m, $SCH_2$, 2H), 0.86 (t, J=7 Hz, $CH_3$, 3H); IR 1741, 1637, 1462, 1319, 1234, 1178, 1132, 1057 cm$^{-1}$;

Anal. Calcd. for $C_{17}H_{12}ClF_4NOS$: C, 52.38; H, 3.10; N, 3.73. Found: C, 52.16; H, 3.19; N, 3.65;

HRMS/ESI $C_{17}H_{11}OF_4N^{35}ClS$ (M–H)$^-$; 388.020238 found: 388.0202 (δ=4.2ppm).

EXAMPLE 18

3-[5-Chloro-2-[(2-methylphenylmethyl)thiolphenyl]-1,3-dihydro-3-fluoro-6-(trifluoromethyl)-2H-indol-2-one; ($R^5$ is 2-methylphenylmethyl)

MS m/e 464 (M–H)$^-$.

EXAMPLE 19

3-[5-Chloro-2-(2-methyl-1-propylthio)phenyl]-1,3-dihydro-3-fluoro-6-(trifluoromethyl)-2H-indol-2-one; ($R^5$ is $CH_3CH(CH_3)CH_2$)

MS m/e 416 (M–H)$^-$.

EXAMPLE 20

3-[5-Chloro-2-(1-propylthio)phenyl]-1,3dihydro-3-fluoro-6-(trifluoromethyl)-2H-indol-2-one; ($R^5$ is $CH_3CH_2CH_2$)

MS m/e 402 (M–H)$^-$.

EXAMPLE 21

3-[5-Chloro-2-(2,5-difluorophenylmethylthio)phenyl]-1,3-dihydro-3-fluoro-6-(trifluoromethyl)-2H-indol-2-one; ($R^5$ is 2,5-difluorophenylmethyl)

MS m/e 489 (M–H)$^-$.

EXAMPLE 22

3-[5-Chloro-2-(3-chloro-1-propylthio)phenyl]-1,3-dihydro-3-fluoro-6-(trifluoromethyl)-2H-indol-2-one; ($R^5$ is $ClCH_2CH_2CH_2$)

MS m/e 437 (M–H)$^-$.

EXAMPLE 23

(±)-3-[5-Chloro-2-(2,2,2-trifluoroethoxy)phenyl]-1,3-dihydro-3-fluoro-6-[4-(trifluoromethyl)phenyl]-2H-indol-2-one mp 103–105° C.; MS m/e 502 (M–H)$^-$

What is claimed is:

1. A compound of Formula I

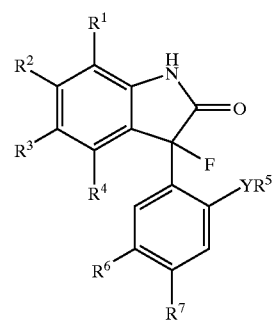

wherein
$R^1$, $R^2$, $R^3$ and $R^4$ each are independently hydrogen, $C_{1-4}$ alkyl, halogen, fluoromethyl, trifluoromethyl, phenyl, 4-methylphenyl or 4-trifluoromethylphenyl;
$R^5$ is $C_{1-6}$ alkyl optionally substituted with one to three same or different groups selected from fluoro and chloro, provided $R^5$ is not $C_{1-6}$ alkyl when Y is O;

Y is O or S; and

R[6] and R[7] each are independently hydrogen, chloro, bromo or trifluoromethyl.

2. The compound of claim 1 which is the (+) enantiomer of a compound as defined in claim 1.

3. The compound of claim 1 wherein Y is O, and R[5] is $C_{1-6}$ alkyl substituted with one to three same or different groups selected from fluoro and chloro.

4. The compound of claim 2 wherein R[5] is $CH_2CF_3$ or $CH_2CH_2F$; R[6] is chloro; and R[7] is hydrogen or chloro.

5. The compound of claim 1 wherein Y is S; R[1], R[3], R[4] and R[7] are hydrogen; R[2] is trifluoromethyl; and R[6] is chloro.

6. The compound of claim 1 selected from the group consisting of:

(±)-3-[5-chloro-2-[(2,2,2-trifluoroethoxy)phenyl]-1,3-dihydro-3-fluoro-6-(trifluoromethyl)-2H-indol-2-one;

(+)-3-[5-chloro-2-[(2,2,2-trifluoroethoxy)phenyl]-1,3-dihydro-3-fluoro-6-(trifluoromethyl)-2H-indol-2-one;

(±)-3-[5-chloro-2-(2,2,2-trifluoroethoxy)phenyl]-1,3-dihydro-3,6-difluoro-2H-indol-2-one;

(±)-3-[5-chloro-2-(2,2,2-trifluoroethoxy)phenyl]-1,3-dihydro-3-fluoro-6-(fluoromethyl)-2H-indol-2-one;

(±)-3-[5-chloro-2-(2,2,2-trifluoroethoxy)phenyl]-4,6-dichloro-1,3-dihydro-3-fluoro-2H-indol-2-one;

(±)-3-[5-chloro-2-(2,2,2-trifluoroethoxy)phenyl]-5,6-dichloro-1,3-dihydro-3-fluoro-2H-indol-2-one;

(±)-3-[5-chloro-2-(2,2,2-trifluoroethoxy)phenyl]-1,3-dihydro-3,5,6-trifluoro-2H-indol-2-one;

(±)-6-chloro-3-[5-chloro-2-(2,2,2-trifluoroethoxy)phenyl]-1,3-dihydro-3-fluoro-2H-indol-2-one;

(+)-6-chloro-3-[5-chloro-2-(2,2,2-trifluoroethoxy)phenyl]-1,3-dihydro-3-fluoro-2H-indol-2-one;

(±)-3-[5-chloro-2-(2-fluoroethoxy)phenyl]-1,3-dihydro-3-fluoro-6-(trifluoromethyl)-2H-indol-2-one;

(±)-3-[4,5-Dichloro-2-(2-fluoroethoxy)phenyl]-1,3-dihydro-3-fluoro-6-(trifluoromethyl)-2H-indol-2-one;

3-[5-chloro-2-(ethylthio)phenyl]-1,3-dihydro-3-fluoro-6-(trifluoromethyl)-2H-indol-2-one;

3-[5-chloro-2-(2-methyl-1-propylthio)phenyl]-1,3-dihydro-3-fluoro-6-(trifluoromethyl)-2H-indol-2-one;

3-[5-chloro-2-(1-propylthio)phenyl]-1,3-dihydro-3-fluoro-6-(trifluoromethyl)-2H-indol-2-one; and (±)-3-[5-chloro-2-(2,2,2-trifluoroethoxy)phenyl]-1,3-dihydro-3-fluoro-6-[4-(trifluoromethyl)phenyl]-2H-indol-2-one.

7. A pharmaceutical composition for the treatment of disorders responsive to opening of KCNQ potassium channels comprising a therapeutically effective amount of the compound of claim 1 in association with a pharmaceutically acceptable carrier, adjuvant or diluent.

8. A pharmaceutical composition for the treatment of disorders responsive to opening of KCNQ potassium channels comprising a therapeutically effective amount of the compound of claim 2 in association with a pharmaceutically acceptable carrier, adjuvant or diluent.

9. A method for the treatment of disorders responsive to opening of the KCNQ potassium channels in a mammal in need thereof, which comprises administering to said mammal a therapeutically effective amount of the compound of claim 1.

10. A method for the treatment of disorders responsive to opening of the KCNQ potassium channels in a mammal in need thereof, which comprises administering to said mammal a therapeutically effective amount of the compound of claim 2.

11. A method of claim 9 wherein said disorder is migraine.

12. A method of claim 10 wherein said disorder is migraine.

* * * * *